United States Patent
Monnard (10) Patent No.: US 12,111,328 B2
(45) Date of Patent: Oct. 8, 2024

(54) METHOD FOR CLASSIFYING AN IDENTIFICATION TAG ON A SAMPLE TUBE CONTAINING A SAMPLE AND AN AUTOMATED LABORATORY SYSTEM

(71) Applicant: Roche Diagnostics Operations, Inc., Indianapolis, IN (US)

(72) Inventor: René Henri Monnard, Zug (CH)

(73) Assignee: Roche Diagnostics Operations, Inc., Indianapolis, IN (US)

(*) Notice: Subject to any disclaimer, the term of this patent is extended or adjusted under 35 U.S.C. 154(b) by 289 days.

(21) Appl. No.: 17/658,951

(22) Filed: Apr. 12, 2022

(65) Prior Publication Data

US 2022/0334141 A1    Oct. 20, 2022

(30) Foreign Application Priority Data

Apr. 19, 2021 (EP) ..................... 21169169

(51) Int. Cl.
*G01N 35/00* (2006.01)
*G06F 18/20* (2023.01)
(Continued)

(52) U.S. Cl.
CPC ....... *G01N 35/00732* (2013.01); *G06N 5/022* (2013.01); *B01L 2200/00* (2013.01);
(Continued)

(58) Field of Classification Search
CPC .............. B01L 2200/00; B01L 2200/14; B01L 2200/143; B01L 2300/00; B01L 2300/02;
(Continued)

(56) References Cited

U.S. PATENT DOCUMENTS 9,230,140 B1    1/2016 Ackley
10,325,182 B2 *  6/2019 Soomro ................. G06V 10/25
(Continued)

FOREIGN PATENT DOCUMENTS

| | | |
|---|---|---|
| EP | 2246689 B1 | 3/2013 |
| WO | 2016/133903 A2 | 8/2016 |
| WO | 2017/157784 A1 | 9/2017 |

OTHER PUBLICATIONS

Nachtrieb, John, "Predicting Scanning Success From Symbol Grade", Barcode Test, Jul. 18, 2018, <https://barcode-test.com/301/predicting-scanning-success-from-symbol-grade> (Year: 2018).*

(Continued)

*Primary Examiner* — Jonathan M Dunlap
(74) *Attorney, Agent, or Firm* — Thomas E. Lees, LLC (57) ABSTRACT

A method for classifying an identification tag on a sample tube containing a sample to be processed in an automated laboratory system having a plurality of laboratory devices, the method comprising providing a sample tube having an identification tag and containing a sample to be analyzed. Each of the plurality of laboratory devices is assigned a tag reader device configured to read the identification tag for recognizing identification tag information. Further, an automated laboratory system for processing a sample tube containing a sample for at least one of pre-analytics and sample analysis is provided.

14 Claims, 2 Drawing Sheets

(51) Int. Cl.

| | | |
|---|---|---|
| *G06F 18/24* | (2023.01) | |
| *G06K 5/02* | (2006.01) | |
| *G06K 5/04* | (2006.01) | |
| *G06K 7/14* | (2006.01) | |
| *G06K 17/00* | (2006.01) | |
| *G06N 5/022* | (2023.01) | |
| *G06N 20/00* | (2019.01) | |
| *G06Q 10/087* | (2023.01) | |
| *G06V 10/70* | (2022.01) | |
| *G06V 10/764* | (2022.01) | |
| *G16H 10/40* | (2018.01) | |
| *G16H 10/60* | (2018.01) | |
| *G16H 10/65* | (2018.01) | |
| *G16H 40/20* | (2018.01) | |

(52) U.S. Cl.
CPC ..... *B01L 2200/14* (2013.01); *B01L 2200/143* (2013.01); *B01L 2300/00* (2013.01); *B01L 2300/02* (2013.01); *B01L 2300/021* (2013.01); *G01N 35/00613* (2013.01); *G01N 35/00722* (2013.01); *G01N 2035/00742* (2013.01); *G01N 2035/00752* (2013.01); *G01N 2035/00762* (2013.01); *G01N 2035/00772* (2013.01); *G06F 18/20* (2023.01); *G06F 18/24* (2023.01); *G06F 18/24765* (2023.01); *G06K 5/02* (2013.01); *G06K 5/04* (2013.01); *G06K 7/1413* (2013.01); *G06K 17/0025* (2013.01); *G06N 20/00* (2019.01); *G06Q 10/087* (2013.01); *G06T 2207/30* (2013.01); *G06T 2207/30204* (2013.01); *G06T 2207/30208* (2013.01); *G06V 10/70* (2022.01); *G06V 10/764* (2022.01); *G06V 10/765* (2022.01); *G16H 10/40* (2018.01); *G16H 10/60* (2018.01); *G16H 10/65* (2018.01); *G16H 40/20* (2018.01)

(58) Field of Classification Search
CPC ........ B01L 2300/021; G01N 35/00613; G01N 35/00722; G01N 35/00732; G01N 2035/00742; G01N 2035/00752; G01N 2035/00762; G01N 2035/00772; G06F 18/00; G06F 18/20; G06F 18/24; G06F 18/24765; G06K 5/00; G06K 5/02; G06K 5/04; G06K 7/1413; G06K 17/0025; G06N 5/022; G06N 20/00; G06Q 10/087; G06T 2207/30; G06T 2207/30204; G06T 2207/30208; G06V 10/00; G06V 10/70; G06V 10/764; G06V 10/765; G16H 40/20

See application file for complete search history.

(56) References Cited

U.S. PATENT DOCUMENTS

| | | | |
|---|---|---|---|
| 10,824,832 B2* | 11/2020 | Kluckner | G06K 7/1491 |
| 11,313,869 B2* | 4/2022 | Tian | G06V 30/19173 |
| 11,386,291 B2* | 7/2022 | Kluckner | G06F 18/24133 |
| 11,538,159 B2* | 12/2022 | Kluckner | G06F 18/22 |
| 2017/0111523 A1* | 4/2017 | Ackley | G06K 19/06037 |
| 2018/0033256 A1* | 2/2018 | Hamidat | G06K 7/1447 |
| 2018/0046883 A1* | 2/2018 | Soomro | G06T 7/11 |
| 2018/0239936 A1* | 8/2018 | Kluckner | G06V 10/44 |
| 2020/0075137 A1* | 3/2020 | Birrer | G16H 10/40 |

OTHER PUBLICATIONS

ATRAS—Registration & Sorting of samples for highest efficiency, Your Solution for the Sample Reception Area and Preanalytics, T&O LabSystems Gmbh & Co. KG, 2021, retrieved from https://web.archive.org/web/20210302130622/https:/to-labsystems.com/en/atras-en/, 7 pp.
ATRAS—Registration and Sorting of Laboratory Samples, T&O LabSystems GmbH & Co. KG, 2021, 6 pp, Screenshots from https://www.youtube.com/watch?v=5tjxe6lpcnY.
Do, Thao et al., Smart Inference for Multidigit Convolutional Neural Network based Barcode Decoding, 25th International Conference on Pattern Recognition, 2020, pp. 3019-3026.
European Search Report issued Oct. 15, 2021, in Application No. 21169169.6, 4 pp.
Fridborn, Fredrick, Reading Barcodes with neural networks, Master of Science Thesis in Electrical Engineering, Department of Electrical Engineering, Linkoping University, 2017, 47 pp.
New TEMPUS600New TEMPUS600® Necto in 2021, Sarstedt AG & Co. KG, 2021, 3 pp., retrieved from https://www.tempus600.com/news/news/new-tempus600%C2%AE-necto -in-2021?Action=1&PID=4787.
Tempus600® Point-to-point transportation of small clinical samples, Predictable and faster transportation time for small clinical samples, Sarstedt AG & Co. KG, 2021, 12 pp.

\* cited by examiner

METHOD FOR CLASSIFYING AN IDENTIFICATION TAG ON A SAMPLE TUBE CONTAINING A SAMPLE AND AN AUTOMATED LABORATORY SYSTEM

CROSS-REFERENCE TO RELATED APPLICATIONS

This application claims priority to European Patent Application No. 21169169.6, filed 19 Apr. 2021, the disclosure of which is hereby incorporated by reference in its entirety.

TECHNICAL FIELD

The present disclosure refers to a method for classifying an identification tag on a sample tube containing a sample to be processed in an automated laboratory system, and an automated laboratory system.

BACKGROUND

A sample tube containing a sample such as a sample of a bodily fluid may be processed or handled in an automated laboratory system for at least one of pre-analytics and sample analysis. For correctly handling or processing the sample tube by the laboratory devices of the automated laboratory system, the sample tube is provided with an identification tag, which, for example, is having a barcode, but may also be provided with some other data matrix code such as QR-code readable by an optical reader.

The identification tag provided on a sample tube in general uniquely identifies the sample tube. Through normal, everyday use, characteristics or conditions of the identification tag such as the barcode may deteriorate, including tearing, peeling, discovering and other deformations. Such deformation may hinder the automated laboratory system from correctly handling or processing the sample tube.

SUMMARY

Although the embodiments of the present disclosure are not limited to specific advantages or functionality, it is noted that in accordance with the present disclosure a method is provided for classifying an identification tag on a sample tube containing a sample to be processed in an automatic laboratory system and an automatic laboratory system, which provide for improved efficiency of processing sample tubes in the automatic laboratory system, and which may be configured for at least one of pre-analytics and sample analysis.

In accordance with one embodiment of the instant disclosure, a method for classifying an identification tag on a sample tube containing a sample to be processed in an automated laboratory system is provided, the method comprising providing a sample tube having an identification tag and containing a sample to be analyzed in an automated laboratory system having a plurality of laboratory devices and, each of the plurality of laboratory devices, having assigned a tag reader device configured to read the identification tag for recognizing identification tag information; and the method further comprising, in a classifying device, providing a classifying module configured to predict, for each of the plurality of laboratory devices, whether the identification tag information can be recognized from measured tag data detected by the tag reader device assigned to the laboratory device and being indicative of characteristics of the identification tag; reading the identification tag on the sample tube by a classifying reader device of the classifying device, thereby, providing the measured tag data for the identification tag indicative of tag characteristics of the identification tag on the sample tube; determining the tag characteristics for the identification tag from the measured tag data; in the classifying module, receiving the tag characteristics, and predicting whether the tag reader device of at least one of the plurality of laboratory devices can read the identification tag; and providing classification data being first classification data indicative of predicting, by the classifying module, the identification tag being readable by the tag reader device of at least one of the plurality of laboratory devices; and second classification data which are different from the first classification data and indicative of predicting, by the classifying module, the identification tag being not readable by the tag reader device of at least one of the plurality of laboratory devices.

In accordance with another embodiment of the instant disclosure, an automated laboratory system for processing a sample tube containing a sample for at least one of pre-analytics and sample analysis is provided, comprising: a sample tube having an identification tag and containing a sample to be processed for at least one of pre-analytics and sample analysis; a plurality of laboratory devices each having assigned a tag reader device configured to read the identification tag; and a classifying device configured to provide a classifying module configured to predict, for each of the plurality of laboratory devices, whether the identification tag can be recognized from measured tag data detected by the tag reader device assigned to the laboratory device and being indicative of characteristics of the identification tag; read the identification tag on the sample tube by a classifying reader device, thereby, providing the measured tag data for the identification tag indicative of tag characteristics of the identification tag on the sample tube; determine the tag characteristics for the identification tag from the measured tag data; in the classifying module, receive the tag characteristics, and predict whether the tag reader device of at least one of the plurality of laboratory devices can read the identification tag; and provide classification data being first classification data indicative of predicting, by the classifying module, the identification tag being readable by the tag reader device of at least one of the plurality of laboratory devices; and second classification data which are different from the first classification data and indicative of predicting, by the classifying module, the identification tag being not readable by the tag reader device of at least one of the plurality of laboratory devices.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numbers and in which.

Skilled artisans appreciate that elements in the figures are illustrated for simplicity and clarity and have not been drawn to scale. For example, dimensions of some of the elements in the figures may be exaggerated relative to other elements to help improve understanding of the embodiment(s) of the present disclosure.

DETAILED DESCRIPTION

According to one embodiment, a method for classifying an identification tag on a sample tube containing a sample to be processed in an automated laboratory system is provided, the method comprising providing a sample tube having an identification tag and containing a sample to be analyzed in an automated laboratory system having a plurality of laboratory devices and, each of the plurality of laboratory devices, having assigned a tag reader device configured to read the identification tag for recognizing identification tag information; and the method further comprising, in a classifying device, providing a classifying module configured to predict, for each of the plurality of laboratory devices, whether the identification tag information can be recognized from measured tag data detected by the tag reader device assigned to the laboratory device and being indicative of characteristics of the identification tag; reading the identification tag on the sample tube by a classifying reader device of the classifying device, thereby, providing the measured tag data for the identification tag indicative of tag characteristics of the identification tag on the sample tube; determining the tag characteristics for the identification tag from the measured tag data; in the classifying module, receiving the tag characteristics, and predicting whether the tag reader device of at least one of the plurality of laboratory devices can read the identification tag; and providing classification data being first classification data indicative of predicting, by the classifying module, the identification tag being readable by the tag reader device of at least one of the plurality of laboratory devices; and second classification data which are different from the first classification data and indicative of predicting, by the classifying module, the identification tag being not readable by the tag reader device of at least one of the plurality of laboratory devices.

According to another embodiment, an automated laboratory system for processing a sample tube containing a sample for at least one of pre-analytics and sample analysis is provided, comprising: a sample tube having an identification tag and containing a sample to be processed for at least one of pre-analytics and sample analysis; a plurality of laboratory devices each having assigned a tag reader device configured to read the identification tag for recognizing identification tag information; and a classifying device. The classifying device is configured to: predict, for each of the plurality of laboratory devices, whether the identification tag information can be recognized from measured tag data detected by the tag reader device assigned to the laboratory device and being indicative of characteristics of the identification tag; read the identification tag on the sample tube by a classifying reader device, thereby, providing the measured tag data for the identification tag indicative of tag characteristics of the identification tag on the sample tube; determine the tag characteristics for the identification tag from the measured tag data, in the classifying module, receive the tag characteristics, and predict whether the tag reader device of at least one of the plurality of laboratory devices can read the identification tag; and provide classification data being first classification data indicative of predicting, by the classifying module, the identification tag being readable by the tag reader device of at least one of the plurality of laboratory devices; and second classification data which are different from the first classification data and indicative of predicting, by the classifying module, the identification tag being not readable by the tag reader device of at least one of the plurality of laboratory devices.

Based on the technology proposed a sample tube to be processed or handled in an automated laboratory system is classified as being a sample tube with an identification tag which can be read by a tag reader of at least one of the plurality of laboratory devices of the automated laboratory system in a way that the identification tag information provided by the identification tag can be recognized for the at least one of the plurality of laboratory devices, or not. If not, the identification tag of the sample tube may not be readable at all or not readable in a way that the identification tag information can be recognized as it would be necessary for correctly handling or processing the sample tube by the automated laboratory system. The identification tag may not be readable at all by at least one of the tag readers each assigned to at least one of the laboratory devices. Alternatively, the identification tag may be readable in part by the tag reader device, but the identification tag information may at least in part not be recognizable from the measured data read for the identification tag. Thus, also in such case the identification may be classified as not readable.

The identification tag information recognizable from reading the identification tag may comprise at least one of sample information for the sample received in the sample tube and sample tube information for the sample tube containing the sample.

Thus, prior to (further) handling or processing the sample tube in the automated laboratory system it can be avoided or prevented that the sample tube is transported or provided to a laboratory device of the automated laboratory system which also may be referred to as instrument of the automated laboratory system if it is predicted by the classifying device that the identification tag of such sample tube will not be readable in a way to recognize the identification tag information by the tag reader device assigned to such laboratory device (instrument). Prior to providing the sample tube to the automated laboratory system or at an early stage of processing the sample tube in the automatic system, the sample tube is classified as having an identification tag for which the identification tag information can be recognized by reading the identification tag, or not. Such classification is based on a (classifying) prediction for the tag reader devices provided in the automated laboratory system, each of the tag reader devices being assigned to at least one of the laboratory devices (instruments) of the automated laboratory system. The classifying device having the classifying module is configured to provide for each of the tag reader devices a prediction whether the identification tag of a sample tube can be read properly for recognizing the identification tag information.

Based on such classification any further handling or processing of the sample tube can be conducted or controlled in response to what the result of the classification is. In an embodiment, it can even be provided that the sample tube is not transported or provided to the automated laboratory system, since the identification tag of the sample tube is found not to be readable by at least one of the tag reader devices provided in the automated laboratory system. The identification tag may be not readable at all by the tag reader devices, or the identification tag information may not be recognizable from a (non-correct) reading result (measured tag data).

The classification data may be outputted through an output device being part of the classifying device or being connected to the classifying device. The output device may be provided, for example, with a display device and/or a speaker device for outputting video data and audio data, respectively. As an alternative, the output data may be provided to a data interface providing for outputting the output data to some data communication line connected, for example, to a control device of the automated laboratory system.

The tag reader devices of the automated laboratory system may be provided, for example, with an optical reader such as a scanner device.

The laboratory devices of the automated laboratory system may be configured to conduct one or more functionalities provided by the automated laboratory system. For example, a laboratory device may be configured to perform pre-analytics. Alternatively, a laboratory device may be configured to conduct sample analysis for the sample received in the sample tube. Another laboratory device may be configured to transport the sample tube between different laboratory devices configured for at least one of pre-analytics and sample analysis. All or only some of the plurality of laboratory devices may be assigned a tag reader device. A single tag reader device may be assigned to more than one laboratory device.

With respect to second classification data, it may be indicative of predicting, by the classifying module, the identification tag being not readable by all tag reader devices from the plurality of laboratory devices.

In case of providing second classification data indicative of predicting, by the classifying module, the identification tag being not readable by the tag reader device of at least one of the plurality of laboratory devices, the steps of reading the identification tag, determining the tag characteristics, and predicting may be repeated at least once. In such repeated classification an amended threshold for a classification parameter (readable vs. not readable) may be applied which is different from an original threshold for the classification parameter applied in the first classification.

The method may further comprise determining control data configured to control handling of the sample tube by the automated laboratory system according to a mode of handling. First control data indicative of a first mode of handling are determined in response to providing the first classification data, and second control data indicative of a second mode of handling are determined in response to providing the second classification data, the second mode of handling being different from the first mode of handling. In addition to first or second classification data, control data are provided indicating a first or second mode of handling or processing for the sample tube in the automated laboratory system. For example, the control data may be indicating that the sample tube for which the identification tag has been read by the classifying reader device is to be transported or provided to some specific laboratory device only (but not to other laboratory devise of the system) in the process of the handling the sample tube by the automated laboratory system. Alternatively, the control data may be indicating that the sample tube is not to be provided to some other laboratory device for which it was predicted that the tag reader device assigned to such other laboratory device will not be able to read the identification tag in a way that the identification tag information is recognizable.

The different control data may be configured to be processed by a control device of the automated laboratory system, thereby, controlling processing or handling of the sample tube in the automated laboratory system. The control device may control a workflow or transporting flow of the sample device in the automated laboratory system in response to the control data. The control data may be generated or determined at least in part by the classifying device. Alternatively, the control data may be determined or generated by the control device of the automated laboratory system in response to the receiving at least one of the first and second classification data provided by the classifying device.

The determining of the control data may further comprise providing control data indicative of the sample tube being assigned to at least one first mode of handling selected from the following group: transporting the sample tube to one or more laboratory device by a transport device of the automated laboratory system; conducting a workflow processing for the sample tube in the automated laboratory system; applying pre-analytics for the sample tube; and conducting sample analysis for the sample contained in the sample tube by one of the laboratory devices from the plurality of laboratory devices. According to the second mode of handling processing or handling of the sample tube may be limited to laboratory devices for which it was predicted that the tag reader device will be able to read the identification tag.

The determining of the control data may further comprise providing control data indicative of the sample tube being assigned to at least one second mode of handling selected from the following group: rejecting the sample tube from handling by the automated laboratory system; replacing the sample tube; and relabeling the sample tube. In response to one the first classification data and the first control data the sample tube may be rejected and prevented from handling by the automated laboratory system. Alternatively, or in addition, the sample tube may be replaced and/or relabeled in response to the classification indicating that the identification tag information is not readable by the tag reader device of at least one of the plurality of laboratory devices. If in response to the first classification data the first control data are provided or generated, the sample tube will be allowed for handling or processing in the automated laboratory system. For example, the control data may be indicative of providing the sample tube to one or more selected laboratory devices in the automated laboratory system during handling or processing of the sample tube.

With respect to rejecting the sample tube from handling by the automated laboratory system, it may be provided that the sample tube is not to be processed (rejected) if not more than about 90% of the tag reader devices assigned to the plurality of laboratory devices can read the identification tag. Alternatively, the sample tube may not be processed if not more than about 80% or 70% or 60% of the tag reader devices can read the identification tag.

Further, with respect to rejecting the sample tube from handling by the automated laboratory system, a sample tube may still not be processed even if it is determined that the tag reader device of a laboratory device providing for some first measurement or analysis can read the identification tag, but not the tag reader device of another laboratory device providing for some second measurement or analysis which is linked to the first measurement or analysis. For example, the first measurement or analysis may be necessary to be conducted prior to the second measurement or analysis which, for example, needs a measurement result of the first measurement or analysis as an input. Such finding could also prevent the two laboratory device from being part of the workflow for processing for the sample tube.

The determining of the control data may further comprise providing workflow data indicative of the workflow processing for the sample tube in the automated laboratory system, and conducting the workflow processing for the sample tube according to the workflow data. The workflow may be determined to be free of some or all laboratory devices for which it is predicted that the tag reader device of such laboratory devices cannot read the identification tag. For example, the automated laboratory system may comprise two or more laboratory devices providing for the same or similar functionality with respect to at least one of sample pre-analytical laboratory and sample analysis. In the course of determining the workflow (data) from such plurality of laboratory devices a laboratory device may be selected to be part of the workflow for which it is predicted that the identification tag can be read by the tag reader device assigned to such laboratory device. Thus, optimized workflow management can be conducted in dependence on the classification data.

The method may further comprise at least one of (i) providing first laboratory device data identifying at least a first laboratory device from the plurality of laboratory devices for which the identification tag is predicted being readable by the tag reader device of at least one first laboratory device; and (ii) providing second laboratory device data identifying at least one second laboratory device from the plurality of laboratory devices for which the identification tag is predicted not being readable by the tag reader device of at least one second laboratory device. In addition to general classification indicated by first or second classification data, first and/or second laboratory device data are provided which is identifying at least a first and/or a second laboratory device for which it is predicted that the identification tag is readable, or not. There may be a list of first laboratory devices indicated by the first laboratory device data providing for a list of laboratory devices for which the identification tag was found to be readable the tag reader device assigned to such first laboratory devices. Similarly, a list of second laboratory devices may be provided by the second laboratory device data indicating a plurality of second laboratory devices for which it is predicted that the identification tag is not readable by the tag reader device assigned to such second laboratory devices. In the process of determining a plurality of first or second laboratory devices, a result of prediction (identification tag information recognizable by reading, or not) may be applied to another laboratory device which is assigned the same tag reader device or which it is assigned a tag reader device providing the same reading procedure like the tag reader device assigned to another laboratory device. Prediction as to whether the identification tag information is recognizable from reading by the tag reader device is made based on identical tag reader characteristics, such tag reader devices, thereby, providing similar results with respect to reading of the identification tag.

The method may further comprise at least one of (i) receiving first update information in the classifying device, the first update information indicating the identification tag being not readable by the tag reader device of the first laboratory while handling the sample tube in the automated laboratory system, and updating the classifying model in response to the first update information; and (ii) receiving second update information in the classifying device, the second update information indicating the identification tag being readable by the tag reader device of the second laboratory while handling the sample tube in the automated laboratory system, and updating the classifying model in response to the second update information. If the prediction made for some laboratory device determined in the course of the classification process is to be found not correct, since there has been contrary result when the sample tube is actually processed or handled in the automated laboratory system, the classifying device is updated by updating the classifying model. For example, a different set of tag characteristics may be defined necessary for reading the identification tag, such tag characteristics assigned to that laboratory device providing the result contrary to the prediction made before for the sample tube. By updating the classifying module a continuously learning or improving classifying device can be provided.

The classifying module may be provided with a machine-learned classifier. The providing of the classifying module may further comprise providing training data for at least a subset of laboratory devices from the plurality of laboratory devices, the training data, for one or more tag reader devices assigned to the subset of laboratory devices, being indicative of (i) first tag characteristics for identification tags on first sample tubes which were recognized from reading the identification tag on the first sample tubes; and (ii) second tag characteristics for identification tags on second sample tubes which were not recognized from reading the identification tag on the second sample tubes. The providing of the classifying module may further comprise conducting a training procedure for the classifying module with the training data, thereby, generating the machine-learned classifier. The machine-learned classifier is trained based on training data indicative of actual reading events conducted for recognizing identification tag information by at least the subset of laboratory devices from the plurality of laboratory devices of the automated laboratory system. For example, if tag reader devices provide for similar reading characteristics for reading identification tags of sample tubes, the subset of laboratory devices does not need to contain historical data (representing reading events) for all laboratory devices of the automated laboratory system. Update information about actual reading events conducted by one or more of the tag reader devices assigned to the laboratory devices may be applied for (additional) training after the classifying device has been in use for some time.

The method may further comprise: providing the classification data to a control device of the automated laboratory system; and controlling handling of the sample tube by the automated laboratory system in dependence on the classification data. In response to receiving the classification data by the control device of the automated laboratory system, control data may be generated for controlling handling of the sample tube according to the classification data. For example, in response to the control data the sample tube may be only provided to one or more laboratory devices of the automated laboratory system for which the identification tag information was predicted to be recognizable (readable) by the tag reader device assigned to such one or more laboratory devices. The sample tube, according to the control data, may be prevented from transporting or providing the sample tube to other laboratory devices for which the identification tag was predicted not to be readable.

The method may further comprise providing the classifying device in at least one of a handheld device, a mobile communication device, and an input device of the automated laboratory system. The handheld device, for example, may be provided by a handheld scanner device such as a barcode or QR code scanner. The mobile communication device for example, may be a mobile phone.

The classifying device may be provided at a point of sample collection separated from the automated laboratory system. Alternatively, the point of sample collection may be provided by an input device of the automated laboratory system. In the different embodiments, the classifying device may be communicatively connectable to the automated laboratory system, for example, to the control device of the automated laboratory system. The classifying device may be implemented in or by an automated pre-analytical laboratory system or an automated analytical laboratory system configured to conduct analysis of the sample received in the sample tube.

The providing of sample tube may comprise at least one of providing a sample tube to be processed in an automated pre-analytical laboratory system and providing a sample tube to be processed in an automated analytical laboratory system. The automated laboratory system may be provided as an automated connected laboratory system. In the connected laboratory system data processors assigned to the laboratory devices may be provided in a cloud data system allowing for sharing and exchanging data among the plurality of laboratory devices.

With respect to the automated laboratory system, the embodiments described above with respect to the method for classifying the identification tag on the sample tube may be applied mutatis mutandis.

In order that the embodiments of the present disclosure may be more readily understood, reference is made to the following examples, which are intended to illustrate the disclosure, but not limit the scope thereof.

Figure 1:
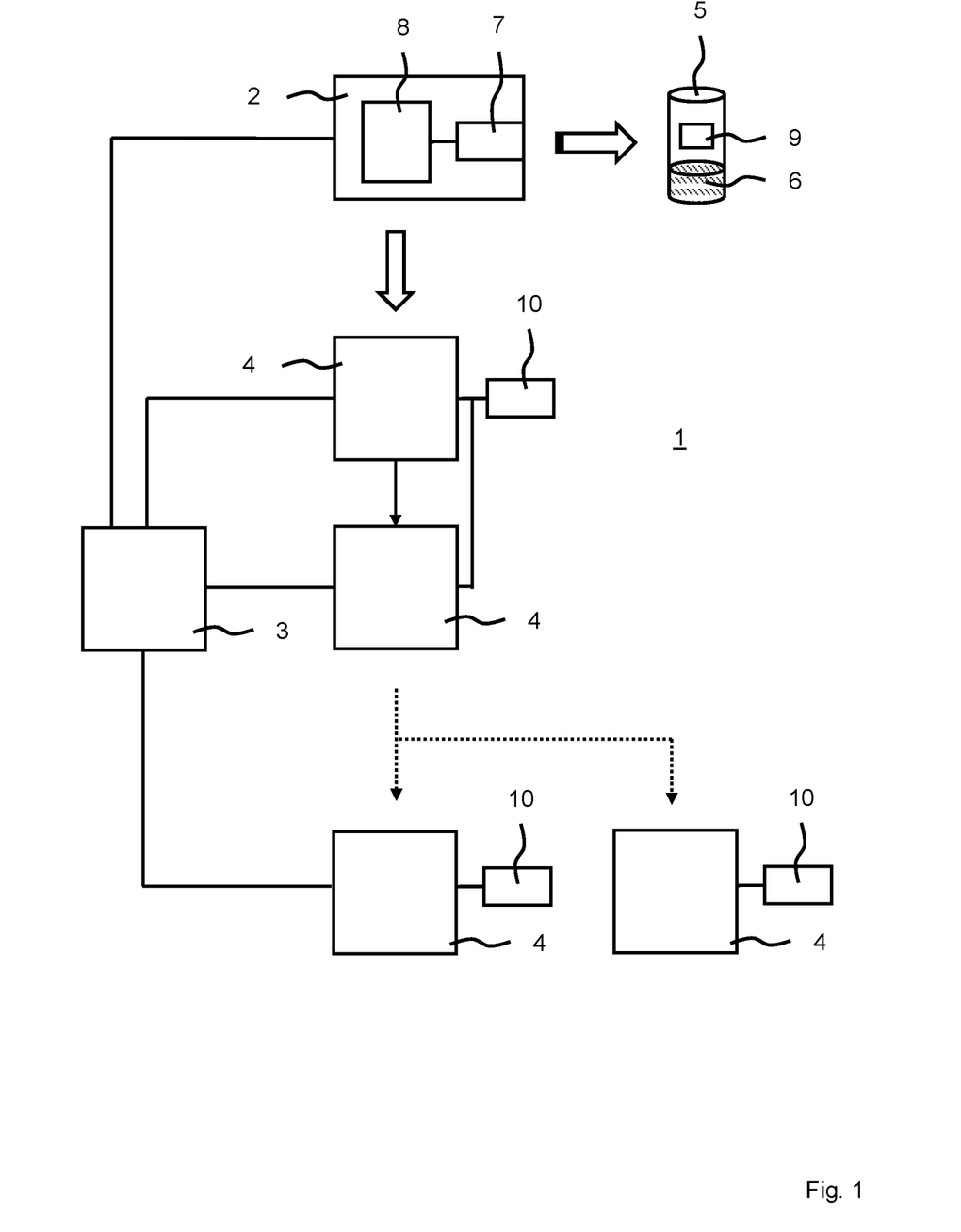
FIG. 1 is a schematic representation of an automated laboratory system configured to process or handle sample tubes containing a sample for applying at least one of pre-analytics and sample analysis in accordance with an embodiment of the present disclosure.

FIG. 1 shows schematic representation of an arrangement having an automated laboratory system 1 and a classifying device 2, for data communication, communicatively connectable to at least a control device 3 of the automated laboratory system 1. Alternatively, the classifying device 2 may be implemented by an instrument of the automated laboratory system 1, for example, by an input laboratory device or instrument such as a point of sample collection.

The automated laboratory system 1 is provided with a plurality of laboratory devices 4 configured to process a sample tube 5 containing a sample 6 for at least one of pre-analytics and sample analysis. The automated laboratory system 1 may be configured for processing a biological or chemical sample. For example, the automated laboratory system 1 may be configured for analysis samples of one or more bodily fluids.

The classifying device 2 can be provided by a separate module in the automated laboratory system 1. Alternatively, the classifying device 2 can be part of a pre-analytics device of the automated laboratory system 1. For example, the classifying device 2 can be provided in a sample check module (not shown). A sample check module as such is known, for example, from European Patent No. 2 246 689 A1.

The plurality of laboratory devices 4 together with the classifying device 2 may be provided in a connected laboratory which, for example, provides for exchanging and sharing data among the plurality of laboratory devices 4 and the classifying device 2. For conducting such data communication and data processing, the plurality of laboratory devices 4 and the classifying device 2 each are provided with one or more data processors, a data memory, and a data communication device as it is known as such. Data communication may be conducted by at least one of wireless data communication and wired data communication.

The sample tube 5 may be transported between the laboratory devices of the plurality of laboratory devices 4 by a transport system (not shown) as it is known as such. One or more sample tubes may be placed in rack for transporting.

The classifying device 2 comprises a classifying reader device 7 and a classifying module 8. The classifying reader device 7 is configured to read an identification tag 9 on the sample tube 5, for example, by means of optical reading. The identification tag 9 may be provided, for example, with a barcode or a QR code. The identification tag 9 is configured to uniquely identify the sample tube 5 containing the sample 6.

Because of normal, everyday use, the condition of the identification tag 9 may deteriorate, including tearing, peeling, discolouring, and other deformations. Because of such deterioration, identification tag information provided by the identification tag 9 may not be recognizable from reading the identification tag 9. The classifying device 2 is provided for predicting whether the identification tag information can be recognized from reading the identification tag 9 by tag reader devices 10 provided in the automated laboratory system 1 and each assigned to one of the laboratory devices 4.

In operation, at the time of the sample tube 5 arriving at a laboratory device from the plurality of laboratory devices 4, the identification tag 9 will be read, for example by optical reading or scanning, by the tag reader device 10 of the laboratory device 4. Depending on whether the identification tag information can be recognized by the tag reader device 10 from such reading, the sample tube 5 can be correctly processed or handled by the laboratory device to which the tag reader device is assigned.

The tag reader device 10 may be different for each laboratory device 4. Alternatively, the tag reader device 10 for a plurality of or all laboratory devices 4 may by the same. For example, the tag reader devices 10 may be using different reading technology such as LED light sensor, laser light sensor, and/or image-based device. The tag reader devices 10 can be implemented differently in the laboratory devices 4, for example, with respect to at least one of illumination of the identification tag 9 for reading, angle for tag reading, and reading distance between the identification tag 9 and the tag reader device 10. Also, the tag reader devices 10 may be from different suppliers, thereby, providing different types of tag reader devices.

If such identification tag information cannot be recognized from the reading, for example, since the identification tag 9 cannot not be read at all, handling of the sample tube 5 containing the sample 6 by such laboratory device may fail or may be conducted not correctly. For avoiding such situation, the identification tag 9 on the sample tube 5 is read by the classifying reader device 7 of the classifying device 2 in advance, for example, prior to handling the sample tube 5 by one of the plurality of laboratory devices 4. This can be conducted at a point of sample collection. In response to such reading, measured tag data are provided in the classifying device 2, the measured tag data being indicative of characteristics of the identification tag 9. For example, images of the identification tag 9 may be detected by the classifying reader device 7. Following, the images may be processed and analysed by image data analysis or processing conducted by one or more data processors provided in the classifying device 2. Depending on such analysis, the identification tag 9 is classified as it described in further detail by referring to FIG. 2.

Figure 2:
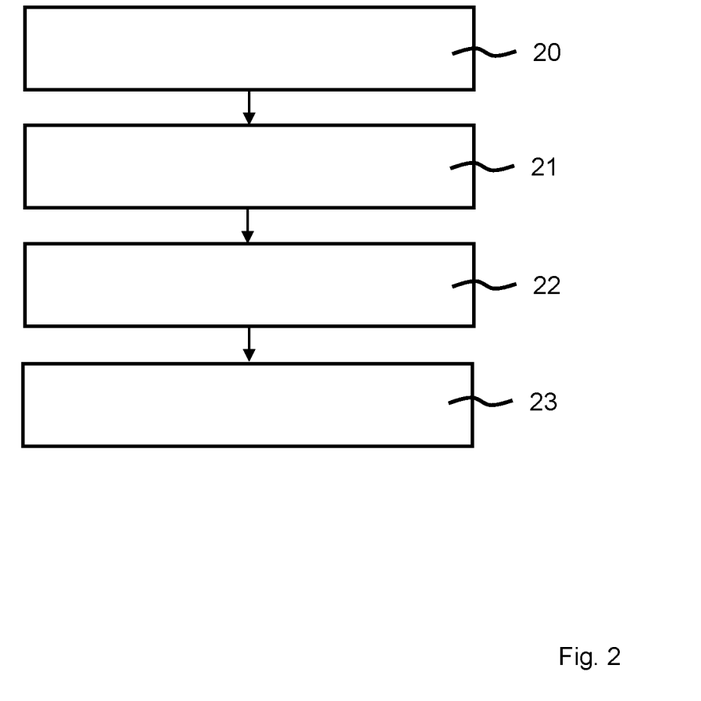
FIG. 2 is a schematic block diagram for a method for classifying an identification tag on a sample tube containing a sample to be processed or handled in the automated laboratory system of FIG. 1 in accordance with an embodiment of the present disclosure.

Referring to FIG. 2, a method for classifying the identification tag 9 on the sample tube 5 is described. In step 20 the identification tag 9 is read by the classifying reader device 7, thereby, generating measured tag data indicative of tag characteristics for identification tag 9. In step 21, by analysing the measured tag data, the tag characteristics which may also be referred to as tag features are determined. For example, the tag characteristics may be indicative of a level of deterioration for the identification tag 9. By means of the classifying module 8 a prediction is made whether the tag reader device 10 of at least one of the plurality of laboratory devices 4 will be able to read the identification tag 9 and recognize the identification tag information from such reading. The identification tag information comprises at least one of sample information for the sample 6 received in the sample tube 5 and sample tube information for the sample tube 5. Sample information, for example, may indicate a type of sample such as sample of blood or a sample of another bodily fluid. Sample tube information, for example, may indicate a type of sample tube and/or a size of the sample tube 5.

By means of the classifying device 2 it will be predicted whether such identification tag information can be recognized by the tag reader device 10 of the plurality of laboratory devices 4. There may be separate prediction result provided for each laboratory device from the plurality of laboratory devices 4. Alternatively, such prediction may be provided only for a subset of laboratory devices from the plurality of laboratory devices 4. For example, information with respect to at least one of pre-analytics and sample analysis may be provided in the classifying device 2, such information indicating one or more laboratory devices (subset of laboratory devices) which will be involved in the processing or handling of the sample tube 5 in the automated laboratory system 1. In such case prediction as to recognisability of the identification tag information from reading of the identification tag 9 needs only to be conducted for such subset of laboratory devices. The prediction may be made on a device-by-device basis (for each of the laboratory devices relevant or selected for the prediction process conducted by the classifying device 2).

In step 23 classification data are generated which at least are indicating whether there is a tag reader device 10 of at least one of the plurality of laboratory devices 4 for which it is predicted that the identification tag 9 is readable by such tag reader device or not. In response to such classification data, the sample tube 5 containing the sample 6 is processed or handled in the automated laboratory system 1. If the classification data are indicating that there is no tag reader device 10 of at least one of the plurality of laboratory devices 4 for which recognisability of the identification tag information is predicted, the sample tube 5 may be rejected from any (further) processing in the automated laboratory system 1. There may be replacement of the sample tube 5. Alternatively or in addition, relabelling may be applied to the sample tube 5, thereby, substituting the identification tag 9. Following, the sample tube 5 with the new identification tag may be classified by the classifying device 2 again.

If the classification data are indicating a tag reader device 5 of at least one of the plurality of laboratory devices 4 being able to recognize the identification tag information from reading the identification tag 9, the sample tube 5 will be provided for further processing by the automated laboratory system 1. For example, the sample tube 5 will be provided to one or more laboratory devices of the plurality of laboratory devices 4. In the cause of such processing at least one of the following may be conducted: Pre-analytics and sample analysis.

The classifying device 2 may be provided with one of the following: A handheld device such as a scanner or optical reader device, a mobile device such as a mobile phone, and an input device of the automated laboratory system 1 such as a stationary input device. Classification of the identification tag 9 on the sample tube 5 may be conducted at a point of sample tube collection, such point of sample tube collection being provided in distance or in close vicinity to the automated laboratory system 1.

The classifying module 8 of the classifying device 2 may be provided with a machine-learned classifier which is trained by a set of training data. The training data may comprise historical data indicative of successful or not-successful reading events conducted by tag reader devices 10 provided in at least one of the automated laboratory system 1 or some other automated laboratory system (not shown). The training data are indicative of reading events allowing for recognizing the identification tag information from reading or not. Based on such historical data the machine-learned classifier can be trained, and following the machine-learned classifier can applied in the classifying module 8. The training data may provide for historical data on a device-by-device basis for the plurality of laboratory devices 5. Thus, in an embodiment, the machine-learned classifier can be trained for the plurality of laboratory devices 4 individually.

The machine-learned classifier provides for predictive modelling for approximating a so-called mapping function from input variables (identification tag characteristics or features) to discrete output variables (identification tag readable or not).

By means of the technology disclosed, different modes of operation can be implemented by the automated laboratory system 1. A first mode may be referred to as "passive mode". This mode of operation can be used at the initiation of the system and measure the accuracy of the classifying module 8 (predictor) by recording the performance of the classifying device 2. A second mode may be referred to as "gatekeeper mode". If the classifying device 2, by the classification data, signals that a sample tube will not be read on one of the instrument of the automated laboratory system 1, the sample tube will be rejected for relabelling. In a third mode which may be referred to as "adaptive mode", some sample tubes that are flagged as non-readable will be allowed in the automated laboratory system 1 to confirm the prediction (or adjust the predictor if the sample can be read).

For classification, the classifying device 2 may apply regression. In an embodiment, the tag reader device 10 of the laboratory device 4 may provide one parameter (e.g., a code readability index). Each tag reader device 10 may apply its own individual threshold limit for deciding whether the identification tag 9 is readable or not by the tag reader device 10. If more than one parameter (or variables) are provided by the classifying device 2, SVM (support vector machine) or CNN (convolutional neural network) may be applied for classification. Image recognition may be applied in a multiple parameter classification. With respect to other parameters (or variables) which may be applied in addition or as an alternative, it may be selected from the following: contrast, brightness, grey levels, multiple colour image, and completeness of bar code in view of the imaging device.

In the different embodiments, by means of the technology disclosed, a plurality of advantageous may be provided. Decision (classification) about readability of the identification tag 9 on the sample tube 5 is based on real performance of the automated laboratory system 1 and not on a reference level. If such an early detection and decision mechanism is implemented using only a reference level then margin has to be built into the system. As an example, if barcode with quality level 3 to 5 (highest) can be read, then the quality level that can be accepted at the input module is 4 to 5. If it is intended this input quality control system can be configured to let in only sample tubes that for sure will be read by all the instruments.

Improved flexibility is provided. The best selection of instrument for the identification tag 9 is defined. Even a similar instrument (laboratory device) might react differently to different identification tag default, and the classifying module 8 learns it.

There is adaptability to reading technology. The technology proposed is technology agnostic. The only important information used from the different instruments in the automated laboratory system 1 is the reading outcome (able or not able to read).

In the end, the technology provides value to the operator of the automated laboratory system 1 which may be implemented as a connected laboratory as early detection produce, in the end, faster results for the sample analysis. It also allow less rework as the classifying device 2 provides a selection based on the real reading performance of each tag reader device 10 in the automated laboratory system 1 and not to an arbitrary detection level. Less rework will also be achieved if the sample tube can be routed to different instrument.

The technology can be used in a automated laboratory system that is not connected, compared to a connected laboratory system, the only difference may be that a technician or user in part would need to follow the instructions provided by the sample tube classification.

What is claimed is:

1. A method for classifying an identification tag on a sample tube containing a sample to be processed in an automated laboratory system, the method comprising providing a sample tube having an identification tag and containing a sample to be analyzed in an automated laboratory system having a plurality of laboratory devices and, each of the plurality of laboratory devices, having assigned a tag reader device configured to read the identification tag for recognizing identification tag information; and the method further comprising, in a classifying device,
   providing a classifying module configured to predict, for each of the plurality of laboratory devices, whether the identification tag information can be recognized from measured tag data detected by the tag reader device assigned to the laboratory device and being indicative of characteristics of the identification tag;
   reading the identification tag on the sample tube by a classifying reader device of the classifying device, thereby, providing the measured tag data for the identification tag indicative of tag characteristics of the identification tag on the sample tube;
   determining the tag characteristics for the identification tag from the measured tag data;
   in the classifying module, receiving the tag characteristics, and predicting whether the tag reader device of at least one of the plurality of laboratory devices can read the identification tag;
   providing first laboratory device data identifying at least a first laboratory device from the plurality of laboratory devices for which the identification tag is predicted being readable by the tag reader device of at least one first laboratory device;
   providing second laboratory device data identifying at least one second laboratory device from the plurality of laboratory devices for which the identification tag is predicted not being readable by the tag reader device of at least one second laboratory device; and
   providing classification data being
      first classification data indicative of predicting, by the classifying module, the identification tag being readable by the tag reader device of at least one of the plurality of laboratory devices; and
      second classification data which are different from the first classification data and indicative of predicting, by the classifying module, the identification tag being not readable by the tag reader device of at least one of the plurality of laboratory devices.

2. The method of claim 1, further comprising determining control data configured to control handling of the sample tube by the automated laboratory system according to a mode of handling, wherein
   first control data indicative of a first mode of handling are determined in response to providing the first classification data; and
   second control data indicative of a second mode of handling are determined in response to providing the second classification data, the second mode of handling being different from the first mode of handling.

3. The method of claim 2, wherein the determining of the control data further comprises providing control data indicative of the sample tube being assigned to at least one first mode of handling selected from the following group:
   transporting the sample tube to one or more laboratory device by a transport device of the automated laboratory system;
   conducting a workflow processing for the sample tube in the automated laboratory system;
   applying pre-analytics for the sample tube; and
   conducting sample analysis for the sample contained in the sample tube by one of the laboratory devices from the plurality of laboratory devices.

4. The method of claim 3, wherein the determining of the control data further comprises providing workflow data indicative of the workflow processing for the sample tube in the automated laboratory system, and conducting the workflow processing for the sample tube according to the workflow data.

5. The method of claim 2, wherein the determining of the control data further comprises providing control data indicative of the sample tube being assigned to at least one second mode of handling selected from the following group:
   rejecting the sample tube from handling by the automated laboratory system;
   replacing the sample tube; and
   relabeling the sample tube.

6. The method of claim 1, further comprising at least one of
   receiving first update information in the classifying device, the first update information indicating the identification tag being not readable by the tag reader device of the first laboratory while handling the sample tube in the automated laboratory system, and updating the classifying model in response to the first update information; and
   receiving second update information in the classifying device, the second update information indicating the identification tag being readable by the tag reader device of the second laboratory while handling the sample tube in the automated laboratory system, and updating the classifying model in response to the second update information.

7. The method of claim 1, wherein the classifying module is provided with a machine-learned classifier and the providing of the classifying module is further comprising
providing training data for at least a subset of laboratory devices from the plurality of laboratory devices, wherein the training data, for one or more tag reader devices assigned to the subset of laboratory devices, are indicative of
first tag characteristics for identification tags on first sample tubes which were recognized from reading the identification tag on the first sample tubes; and
second tag characteristics for identification tags on second sample tubes which were not recognized from reading the identification tag on the second sample tubes; and
conducting a training procedure for the classifying module with the training data, thereby, generating the machine-learned classifier.

8. The method of claim 1, further comprising
providing the classification data to a control device of the automated laboratory system; and
controlling handling of the sample tube by the automated laboratory system in dependence on the classification data.

9. The method of claim 1, further comprising providing the classifying device in at least one of a handheld device, a mobile communication device, and an input device of the automated laboratory system.

10. The method of claim 1, wherein the providing of the sample tube comprises at least one of providing a sample tube to be processed in an automated pre-analytical laboratory system and providing a sample tube to be processed in an automated analytical laboratory system.

11. An automated laboratory system for processing a sample tube containing a sample for at least one of pre-analytics and sample analysis, comprising:
a sample tube having an identification tag and containing a sample to be processed for at least one of pre-analytics and sample analysis;
a plurality of laboratory devices each having assigned a tag reader device configured to read the identification tag; and
a classifying device configured to
provide a classifying module configured to predict, for each of the plurality of laboratory devices, whether the identification tag can be recognized from measured tag data detected by the tag reader device assigned to the laboratory device and being indicative of characteristics of the identification tag;
read the identification tag on the sample tube by a classifying reader device, thereby, providing the measured tag data for the identification tag indicative of tag characteristics of the identification tag on the sample tube;
determine the tag characteristics for the identification tag from the measured tag data;
in the classifying module, receive the tag characteristics, and predict whether the tag reader device of at least one of the plurality of laboratory devices can read the identification tag;
provide first laboratory device data that identifies at least a first laboratory device from the plurality of laboratory devices for which the identification tag is predicted being readable by the tag reader device of at least one first laboratory device;
provide second laboratory device data that identifies at least one second laboratory device from the plurality of laboratory devices for which the identification tag is predicted not being readable by the tag reader device of at least one second laboratory device; and
provide classification data being
first classification data indicative of predicting, by the classifying module, the identification tag being readable by the tag reader device of at least one of the plurality of laboratory devices; and
second classification data which are different from the first classification data and indicative of predicting, by the classifying module, the identification tag being not readable by the tag reader device of at least one of the plurality of laboratory devices.

12. The automated laboratory system of claim 11, provided as one of an automated pre-analytical laboratory system and an automated analytical laboratory system.

13. The automated laboratory system of claim 11, provided as a connected automated laboratory system.

14. The automated laboratory system of claim 11, wherein the classifying device in at least one of a handheld device, a mobile communication device, and an input device of the automated laboratory system.

* * * * *